United States Patent [19]

Deguchi et al.

[11] Patent Number: 5,378,738
[45] Date of Patent: Jan. 3, 1995

[54] BIODEGRADABLE PLASTIC

[75] Inventors: Tetsuya Deguchi; Tomoaki Nishida; Yoshimasa Takahara, all of Tsukuba, Japan

[73] Assignee: Kabushiki Kaisha Kobe Seiko Sho, Kobe, Japan

[21] Appl. No.: 78,296

[22] PCT Filed: Oct. 30, 1992

[86] PCT No.: PCT/JP92/01411
§ 371 Date: Jun. 25, 1993
§ 102(e) Date: Jun. 25, 1993

[87] PCT Pub. No.: WO93/09184
PCT Pub. Date: May 13, 1993

[30] Foreign Application Priority Data

Oct. 31, 1991 [JP] Japan .................................. 3-311550
Mar. 4, 1992 [JP] Japan .................................... 4-81485
Mar. 4, 1992 [JP] Japan .................................... 4-81487

[51] Int. Cl.$^6$ ......................... C08J 11/00; C08K 5/00; C12P 1/04; C12N 1/00
[52] U.S. Cl. .................................. 435/262; 523/128; 523/124; 435/171; 435/254.1
[58] Field of Search .................. 523/124, 128; 524/47, 524/56, 35, 25, 423, 441, 448, 493; 435/170, 171, 262, 254, 243, 252.1; 210/632

[56] References Cited

U.S. PATENT DOCUMENTS

| 4,016,117 | 4/1977 | Griffin | 260/17.4 ST |
| 5,118,725 | 6/1992 | Suominen | 523/122 |

FOREIGN PATENT DOCUMENTS

| 0400532 | 5/1990 | European Pat. Off. . |
| 48-96633 | 3/1972 | Japan . |
| 49-131236 | 4/1973 | Japan . |
| 49-55740 | 5/1973 | Japan . |
| 5057834 | 10/1973 | Japan . |
| 5062243 | 10/1973 | Japan . |
| 50-86543 | 7/1975 | Japan . |
| 3-31333 | 2/1991 | Japan . |
| 3-179036 | 8/1991 | Japan . |
| 3-269059 | 11/1991 | Japan . |

Primary Examiner—Paul R. Michl
Assistant Examiner—LaVonda DeWitt
Attorney, Agent, or Firm—Oblon, Spivak, McClelland, Maier & Neustadt

[57] ABSTRACT

A biodegradable plastic added at an amount of a hydrophilic property imparting-substance providing wettability such that the contact angle of plastic surface to water is 70° or less whereby the decomposability thereof with Basidiomycetes, the cultured products thereof and/or the processed products thereof is improved. A method for decomposing plastic under the conditions with limitation to nitrogen and/or carbon in decomposing such biodegradable plastic. In accordance with the present invention, the plastic which has conventionally been decomposed with difficulty can be decomposed efficiently.

19 Claims, No Drawings

BIODEGRADABLE PLASTIC

INDUSTRIAL FIELD

The present invention relates to a method for decomposing plastic and a decomposing agent therefor as well as a biodegradable plastic.

Therefore, the present invention not only makes greater contribution to the disposal of plastic waste which is now drawing serious social concern, but also proposes the elucidation of the decomposing mechanism thereof and the designing of a biodegradable plastic.

BACKGROUND OF THE INVENTION

Polyolefin plastic has been considered non-biodegradable conventionally, and it has been known that only about 1% of polyethylene as a polyolefin plastic is decomposed after 10-year bacterial treatment (Journal of Applied Polymer Science, 35, 1288–1302 (1988)).

Also, it is known a method for decomposing polyamide plastic by means of a bacterium (Flavobacterium sp. K172) (Agr. Bio Chem., 39 (6), 1219–1223(1975); Hakkoukougakukaishi, 60(5), 363–375(1982)). However, all of these conventional methods concerning polyamide plastic are classified in the method for treating water-soluble, low-molecular nylon 6 oligomer (molecular weight of about 2,000 or less). Thus, water-insoluble, high-molecular nylon (molecular weight of about 10,000 or more) cannot be decomposed with these methods.

It has been known a biodegradable composition which has been modified for ready biological attack by dispersing starch in a thermoplastic synthetic resin (Japanese Patent Laid-open No. Sho 49-55740). In the biodegradable composition, however, it is only the starch particle that is decomposed biologically, whereas the synthetic resin cannot be decomposed. That is, the composition is just degraded when the starch particle is not any more decomposed, so the synthetic resin still remains.

For the disposal of plastic waste, the rapid decomposition of plastic waste of itself is an issue of significance. Therefore, such objective cannot be achieved by the conventional methods, as is apparently shown in what has been described above.

Under such current technical circumstances, the present invention has been performed for the objective to prevent plastic pollution. The present invention has been carried out for the objective to provide a method for efficiently decomposing plastic of itself which has never been substantially decomposed by the conventional methods and to provide a plastic suitable for such decomposition method.

DISCLOSURE OF THE INVENTION

The present inventors have made investigation so as to achieve the aforementioned objectives, and have thus focused their attention to biological treatment by means of a variety of bacteria from the respect of preventing secondary pollution. However, the inventors have recognized the need of conceptual innovation concerning microbial selection, culturing condition, treating condition and the like because they have not been able to achieve the primary objective. Thus, they have made reinvestigation.

By selecting Basidiomycetes as a microorganism, it has been found in accordance with the present invention that enzymes generated from Basidiomycetes cannot act on non-hydrophilic plastic but can act on plastic mixed or coated with a hydrophilic property imparting-substance which can then impart wettability to the plastic whereby the enzymes can sufficiently decompose the plastic of itself.

As to polyolefin plastic in particular, polyolefin plastic after hydrophilic treatment is subjected to bacterial treatment under conditions without supplement of nitrogen source and/or carbon source as essential nutrients for bacterial growth or treatment which conditions are totally contrary to conventional state of the art. It has been found that Basidiomycetes can efficiently decompose polyolefin plastic. Thus, the present invention has been achieved. In the present Specification, polyolefin plastic is often referred to as polyethylene hereinbelow.

BEST MODE OF CARRYING OUT THE INVENTION

Polyethylene, nylon, polypropylene, polyvinyl chloride, polystyrene, polyurethane, polyester and the like are included in plastic and these are decomposable.

These types of plastic are remarkably improved of their decomposition property with Basidiomycetes by molding after these are mixed with a substance imparting hydrophilic property or by coating with a substance imparting hydrophilic property after molding. Plastic form may be either in film or in shape.

The substance imparting hydrophilic property may be added or coated at an amount imparting wettability such that the contact angle of the plastic surface to water is 70° or less, preferably 60° or less.

The substance imparting hydrophilic property illustratively includes hydrophilic organic substances such as starch, processed starch, cereal, mannit, lactose, dextran, cellulose, CMC, casein, higher fatty acids in linear chain, higher alcohols in linear chain, polyethylene glycol, polypropylene glycol, Tween 80, and other various surfactants and the like. Also, the illustrative examples thereof include hydrophilic inorganic substances such as diatomaceous earth, silica, alumina, calcium chloride, magnesium sulfate, sodium sulfate and the like.

The method for producing the biodegradable plastic of the present invention preferably comprises appropriately mixing the plastic in pellets with one or two or more of substances imparting hydrophilic property and molding the mixture following a molding method suitable for an objective molded article, but may also comprise preliminarily adding a hydrophilic substance to a plastic material during the molding process thereof and polymerizing the material. A substance imparting hydrophilic property may also be coated onto the surface of a molded plastic. But in such case, it is recommended to immobilize the substance imparting hydrophilic property to effect coating.

In accordance with the present invention, wettability is essential at a degree such that the enzymes generated from Basidiomycetes may act on the plastic. The amount of a substance to be added for imparting hydrophilic property largely varies depending on each substance, but an amount may be satisfactory if it can impart wettability such that the contact angle of the plastic surface to water is 70° or less, preferably 60° or less. The enzymes generated from Basidiomycetes can act on the plastic imparted with wettability so that various types of plastic can be decomposed directly. The present invention further encompasses a method for decomposing and treating the plastic treated with hydrophilic process so as to impart hydrophilic property or plastic originally having hydrophilic property, by means of Basidiomycetes, the cultured products thereof and/or the processed products thereof. Furthermore, the plastic having hydrophilic property may be decomposed with Basidiomycetes, the cultured products thereof and/or the processed products thereof under the conditions with limitation to nitrogen and/or carbon.

Basidiomycetes may be from natural origin, but such Basidiomycetes is not so abundant to show satisfactory decomposing activity. A decomposing agent containing preliminarily cultured Basidiomycetes in preparation may be sprayed on.

In accordance with the present invention, Basidiomycetes, wood rot Basidiomycetes in particular, may be used frequently, but white rot Basidiomycetes, namely lignin decomposing bacterium, is specifically used advantageously.

Such white rot Basidiomycetes illustratively includes the fungi from the following genera; *Coriolus versicolor*, IFO 7043, etc.; *Phanerochaete chrysosporium*, ACTT 34541, etc.; *Trametes dickinsii*, IFO 6488, etc.; *Polyporus mikadoi*, IFO 6517, etc.; *Stereum frustulosum*, IFO 4932, etc.; *Ganoderma applanatum*, IFO 6499, etc.; *Lenzites betulina*, IFO 8714, etc.; *Fomes fomentarius*, IFO 30371, etc.; *Porodisculus pendulus*, IFO 4967, etc.; *Lentinus edodes*, IFO 31336, *L. lepideus*, IFO 7043, etc.; *Serpula lacrymans*, IFO 8697, etc.; and the like.

In addition to those described above, strain NK-1148 (FERM BP-1859) and strain *Porodisculus pendulus* (strain NK-729W; FERM BP-1860) may satisfactorily be used. The strain NK-1148 is a microorganism isolated by the present inventors and is deposited as FERM BP-1589 in the Patent Microorganism Depository, Fermentation Research Institute, Agency of Industrial Science and Technology, at 1-3, Higashi 1-chome, Tsukuba-shi, Ibaraki-ken, 305, Japan (original deposition date; May 23, 1987). The detailed mycological characteristics thereof are disclosed in Japanese Patent Publication No. Hei 3-32997.

The decomposing agent containing Basidiomycetes is generally produced by inoculating and culturing various Basidiomycetes in wood powder and then preparing the powder into particles, but various liquid cultured products or various solid cultured products may be used appropriately. It is also recommended to use the products from the culture of Basidiomycetes under the conditions with limitation to nitrogen and/or carbon.

Only if the Basidiomycetes agent of the present invention is sprayed onto the plastic waste added with a hydrophilic property imparting-substance whereby the plastic is rendered decomposable with Basidiomycetes, the cultured products thereof and/or the processed products thereof, the plastic is decomposed with Basidiomycetes, the cultured products thereof and/or the processed products thereof, thereby disposing the waste for a short period of time.

The present invention further comprises decomposing polyolefin plastic with one or more of Basidiomycetes described above, and then, it is more efficient to treat the plastic with hydrophilic process or under the conditions with limitation to nitrogen and/or carbon.

More specifically, when polyolefin plastic is made to contact to Basidiomycetes at an optimum temperature, for example, 15° to 35° C., preferably in the state with limitation to nitrogen and/or carbon, polyolefin plastic can be decomposed extremely efficiently at about 5 to 30 days.

In such case, it is important to limit nitrogen and/or carbon in spite of microbial treatment. Nitrogen and/or carbon should be rendered as less as possible. Preferably, nitrogen and/or carbon is not contained therein. From industrial respect, however, the nitrogen concentration should be 0.1 g/l or less. If the concentration is rendered 0.05 g/l, better results can be obtained. The carbon concentration should be 1.0 g/l, and more preferably, the concentration should be 0.2 g/l. With no specific limitation to the nutrients other than nitrogen and carbon, individual components routinely employed for the growth of Basidiomycetes may appropriately be used. If the aforementioned conditions regarding nitrogen and/or carbon are satisfied, the intended objective can be attained in accordance with the present invention. Therefore, polyolefin plastic can be decomposed in the state wherein nitrogen sources and carbon sources are completely eliminated, for example, by adding polyolefin plastic and Basidiomycetes to water for incubation.

In accordance with the present invention, Basidiomycetes is employed, and in addition to the Basidiomycetes of itself, the cultured products thereof and/or the processed products thereof may be employed as well. By the cultured products thereof are broadly meant the mixture of the mycelia obtained by culturing the Basidiomycetes with the culture broth. In accordance with the present invention, the mycelia in the form of such as wet cake separated from the culture, the residue thereof and the culture broth obtained by completely removing the mycelia, may be also employed. Furthermore, the processed products thereof mean all of those obtained by concentrating, drying or diluting those described above. By using the cultured products and processed products of Basidiomycetes cultured with limitation to nitrogen and/or carbon, polyolefin plastic should satisfactorily be decomposed.

In subjecting polyolefin plastic to decomposition process according to the present invention, polyolefin plastic is preferably subjected to hydrophilic process so as to readily contact polyolefin plastic to the microorganisms, enzymes generated therefrom or the like. As the hydrophilic process of polyolefin plastic, use may be made of a method comprising coating and/or mixing surfactants routinely employed, a method comprising coating and/or mixing inorganic matters or organic matters and the like. As a specifically preferable method therefor, a method is recommended, comprising adding a substance imparting hydrophilic property to the surface or inside of plastic to be processed, thereby providing wettability such that the contact angle of the plastic surface to water should be 70° or less, preferably 60° or less. Furthermore, such polyolefin plastic is more preferably powdered or made porous. In accordance with the present invention, any polyolefin plastic can be decomposed other than high-pressure polyethylene, low- and medium-pressure polyethylene, and other various polypropylene. It is needless to say that the mixtures thereof may be biodegradable.

The present invention will now be explained in details with reference to examples, but the present invention is not limited to the following examples. It is to be understood that any modification of the present invention may be encompassed within the technical scope of the present invention, unless departing from the spirit what has been described hereinabove and what will be described hereinafter.

EXAMPLE 1

Placing hydrophilic polyethylene films (HYPORE PE-1100; manufactured by Asahi Kasei, Co. Ltd.) onto a solid medium ($KH_2PO_4$: 1.0 g, $NaH_2PO_4$: 0.2 g, $MgSO_5 \cdot 7H_2O$: 0.1 g, $ZnSO_4 \cdot 7H_2O$: 0.01 mg, $CuSO_4 \cdot 5H_2O$: 0.02 mg, glucose: 20 g, agar: 30 g, water: 1 liter), the inoculation of individual microorganisms (white rot Basidiomycetes; *Phanerochaete chrysosporium* ATCC 34541, *Coriolus versicolor* IFO 7043, NK-1148 FERM BP-1859; brown rot Basidiomycetes; *Lentinus lepideus* IFO 7043, *Serpula lacrymans* IFO EPRI 6352, incomplete fungi; *Aspergillus niger* IFO 6341, *Penicillium citrinum* IFO 6352, bacteria; *Bacillus subtilis* IFO 3134, *Pseudomonas paucimobillis* SYK-6) was done followed by stationary culture at 20° to 28° C. for 20 days. After incubation, the polyethylene films were suspended in water. Biodegradability was evaluated by observation of the suspension state. Furthermore, the polyethylene films highly decomposed by observation were analyzed by GPC (Column KS-80M manufactured by Showa Denko, Co. Ltd., elution solution; TCB, flow rate; 1 ml/min, temperature; 135° C., detector; RI). The biodegradability was assessed through the modification of the average molecular weight. The results are shown in the following Table 1.

TABLE 1

Polyethylene decomposition activity of each microorganism

| Bacterial species | Dispersibility | Weight average molecular weight | Number average molecular weight |
|---|---|---|---|
| Lumber rot Basidiomycetes | | | |
| White rot Basidiomycetes | | | |
| *P. chrysosporium* | + + | | |
| *C. versicolor* | + | | |
| NK-1148 | + + + | 10,000 | 2,000 |
| Brown rot Basidiomycetes | | | |
| *L. lepideus* | + | | |
| *S. lacrymans* | + | | |
| Incomplete fungi | | | |
| *Aspergillus niger* | − | | |
| *Penicillium citrinum* | − | | |
| Bacteria | | | |
| *Bacillus subtilis* | − | | |
| *Ps. paucimobillis* | − | | |

Note-1; Dispersibility
High: + + +
Medium: + +
Low: +
Non dispersible: −
Note-2; Control (without microbial treatment)
Weight average molecular weight 125,000
Number average molecular weight 29,000

As is apparently shown in Table 1, it was confirmed that wood rot Basidiomycetes can decompose polyethylene film. Such films were highly decomposed, specifically when strain NK-1148 was used. GPC analysis showed that polyethylene of a weight average molecular weight of 125,000, which has absolutely never been decomposed conventionally, was decomposed into a weight average molecular weight of 10,300.

EXAMPLE 2

Using the white rot Basidiomycetes (NK-1148) and following the treating conditions as in Example 1, stationery culture was done on a solid medium with a different nitrogen concentration (the same medium composition as in Example 1, except that the nitrogen concentration was adjusted to 0 g/l, 0.05 g/l, 0.10 g/l and 0.15 g/l via ammonium sulfate addition) for assessing the decomposability following Example 1. The results are shown in Table 2.

TABLE 2

Effects of nitrogen concentration in the medium on polyethylene decomposition

| N concentration | Dispersibility |
|---|---|
| 0.15 g/l | − |
| 0.10 g/l | + |
| 0.05 g/l | + + |
| 0.0 g/l | + + + |

Note-1; Dispersibility
High: + + +
Medium: + +
Low: +
Non dispersible: −

EXAMPLE 3

Using the white rot Basidiomycetes (NK-1148) and following the treating conditions as in Example 1, stationery culture was done on a solid medium with a different carbon concentration (the same medium composition as in Example 1, except that the carbon concentration was adjusted to 0 g/l, 0.2 g/l, 0.4 g/l and 8.0 g/l via glucose addition; and nitrogen concentration was adjusted to 0.15 g/l via 0.58 g of ammonium sulfate addition) for assessing the decomposability following Example 1. The results are shown in Table 3.

TABLE 3

Effect of carbon concentration in the medium on polyethylene decomposition

| Carbon concentration | Dispersibility |
|---|---|
| 8.0 g/l | − |
| 0.4 g/l | + |
| 0.2 g/l | + + |
| 0.0 g/l | + + + |

Note-1; Dispersibility
High: + + +
Medium: + +
Low: +
Non dispersible: −

EXAMPLE 4

Using the white rot Basidiomycetes (NK-1148) and following the treating conditions as in Example 1, stationery culture was done on two types of solid media, namely a solid medium without nitrogen and carbon sources (the same medium composition as in Example 1 except that glucose was adjusted to 0 g) and a solid medium produced by removing all of the nutrients from the medium of Example 1 (30 g of agar and 1 liter of water), for assessing the decomposability following Example 1. The results are shown in table 4.

TABLE 4

Effects of medium nitrogen and carbon concentrations on polyethylene decomposition

| Carbon concentration (g/l) | Nitrogen concentration (g/l) | Dispersibility |
|---|---|---|
| 0.0 | 0.0 | + + + |
| 0.0 | 0.0 (All of nutrients removed) | + + + |
| 0.0 | 0.15 | + + + |
| 8.0 | 0.0 | + + + |

TABLE 4-continued

Effects of medium nitrogen and carbon concentrations on polyethylene decomposition

| Carbon concentration (g/l) | Nitrogen concentration (g/l) | Dispersibility |
|---|---|---|
| 8.0 | 0.15 | — |

Note-1; Dispersibility
High: +++
Medium: ++
Low: +
Non dispersible: —

EXAMPLE 5

In the solid medium of the nitrogen concentration at which the maximum decomposition activity in Example 2 was exhibited (at 0 g/l ammonium sulfate and at the other conditions as the same in Example 1), the effect of the hydrophilic process of polyethylene film was examined, by using white rot Basidiomycetes (NK-1148). As samples, use was made of hydrophobic polyethylene film (HYPORE PE-2100 manufactured by Asahi Kasei, Co. Ltd.) and the polyethylene film treated with a surfactant (the hydrophobic film after immersion in an aqueous 0.1% Tween 80 solution for 24 hours) for imparting hydrophilic property. The decomposability was examined by GPC as in Example 1. The results are shown in Table 5.

TABLE 5

Effects of the hydrophilic process of polyethylene on polyethylene decomposition

| Hydrophilic process | Weight average molecular weight | Number average molecular weight |
|---|---|---|
| No | 144,000 | 29,000 |
| Yes | 24,500 | 3,100 |

Note-1; Control (without fungal treatment)
Weight average molecular weight 145,000
Number average molecular weight 29,000

EXAMPLE 6

After mixing 10 parts by weight of nylon 66 in pellets (manufactured by Aldrich) and one part each of various additives for imparting hydrophilic property, i.e. polyethylene glycol (manufactured by WAKO CHEMICALS), polypropylene glycol (manufactured by WAKO CHEMICALS), Tween 80 (manufactured by KISHIDA, Co. Ltd.) and silica (MIZUCASIL P-700 manufactured by MIZUSAWA INDUSTRIAL COMPANY, Co. Ltd.), the resulting mixture was dissolved in 100 parts by weight of hexafluoroisopropanol to make a cast solution. By using a spreader for thin-layer chromatography, the cast solution was uniformly cast on glass surface. Then, hexafluoroisopropanol was removed under reduced pressure to produce a nylon 66 film imparted with hydrophilic property. Also, nylon 66 films without various additives mixed (with no hydrophilic property imparted) were prepared by the same method. The contact angles of these various films to water were measured by liquid-drop method (Polymer Society, Committee of Polymer and Water: Polymer and Water (Saiwai Press)).

These various films were placed on a solid medium ($KH_2PO_4$: 1.0 g, $NaH_2PO_4$: 0.2 g, $MgSO_4 \cdot 7H_2O$: 0.1 g, $ZnSO_4 \cdot 7H_2O$: 0.01 mg, $CuSO_4 \cdot 5H_2O$: 0.02 mg, glucose: 20 g, agar: 30 g, water: 1 liter), followed by the inoculation of white rot Basidiomycetes (NK-1148) for stationery culture at 28° C. for 10 days. After the culture, the nylon 66 films were measured of their molecular weight and assessed of their biodegradability.

The molecular weight distribution was analyzed by high-temperature GPC (150-C manufactured by Waters, Co. Ltd.). The analytical conditions were as follows; columns; Microstylagel HT-linear and Ultrastylagel 500, manufactured by Waters, Co. Ltd., elution solution; m-cresol, flow rate; 1 ml/min temperature; 100° C., detector; RI. The average molecular weights of the samples after such fungal treatment are shown in Table 6.

TABLE 6

| Presence and types of additives | Weight average molecular weight | Number average molecular weight |
|---|---|---|
| No addition (without hydrophilic property imparted) | 151,000 | 25,000 |
| Addition (with hydrophilic property imparted) | | |
| Polyethylene glycol | 50,000 | 5,000 |
| Polypropylene glycol | 63,000 | 7,000 |
| Tween 80 | 54,000 | 6,000 |
| Silica | 66,000 | 8,000 |

Note; Control (without fungal treatment)
Weight average molecular weight 187,000
Number average molecular weight 43,000

EXAMPLE 7

Except for the use of polyethylene with hydrophilic property imparted through silica addition (PE-1100 manufactured by Asahi Kasei, Co. Ltd.) and polyethylene without hydrophilic property imparted (PE-2100 manufactured by Asahi Kasei, Co. Ltd.) and that the incubation period was set at 20 days, the same biodegradability test as in Example 6 was undertaken.

The molecular weight distribution was analyzed by high-temperature GPC (150-C manufactured by Waters, Co. Ltd.). The analytical conditions were as follows; columns; Microstylagel HT-linear and Ultrastylagel 500, manufactured by Waters, Co. Ltd., elution solution; m-cresol, flow rate; 1 ml/min, temperature; 135° C., detector; RI. The average molecular weights of the samples after such fungal treatment are shown in Table 7.

TABLE 7

| Samples | Weight average molecular weight | Number average molecular weight |
|---|---|---|
| Polyethylene without silica added | | |
| Before fungal treatment | 145,000 | 29,000 |
| After fungal treatment | 144,000 | 29,000 |
| Polyethylene with silica added | | |
| Before fungal treatment | 125,000 | 29,000 |
| After fungal treatment | 10,000 | 2,000 |

INDUSTRIAL APPLICABILITY

In accordance with the present invention, plastic can be decomposed efficiently. Also, such highly biodegradable plastic can be provided. Additionally, no secondary pollution is induced. Thus, the present invention makes great contribution to the disposal of plastic waste which is now drawing serious social concern.

What is claimed is:

1. A biodegradable plastic produced by adding a substance imparting hydrophilic property to a plastic material, characterized in that the plastic is decomposed by Basidiomycetes, the cultured products thereof and/or the processed products thereof.

2. A biodegradable plastic according to claim 1, wherein the substance imparting hydrophilic property is a hydrophilic organic substance.

3. A biodegradable plastic according to claim 1, wherein the substance imparting hydrophilic property is a hydrophilic inorganic substance.

4. A biodegradable plastic according to claim 1, having wettability such that the contact angle thereof to water is 70° or less.

5. A biodegradable plastic according to any one of claims 1 to 4, wherein the plastic material is polyolefin plastic.

6. A biodegradable plastic according to any one of claims 1 to 4, wherein the plastic material is polyamide plastic.

7. A method for decomposing plastic wherein polyolefin plastic is decomposed with Basidiomycetes, the cultured products thereof and/or the processed products thereof.

8. A method for decomposing plastic according to claim 7, wherein the polyolefin plastic is decomposed under conditions such that nitrogen concentration is not more than 0.1 g/l and carbon concentration is not more than 1.0 g/l.

9. A method for decomposing plastic comprising adding a substance imparting hydrophilic property to a plastic material and decomposing the material with Basidiomycetes, the cultured products thereof and/or the processed products thereof.

10. A method for decomposing plastic according to claim 9, wherein the plastic material is polyolefin plastic.

11. A method for decomposing plastic according to claim 10, wherein the polyolefin plastic is decomposed under conditions such that nitrogen concentration is not more than 0.1 g/l and carbon concentration is not more than 1.0 g/l.

12. A method for decomposing plastic according to claim 10, comprising preparing the polyolefin plastic into powder or porous film and decomposing the plastic with Basidiomycetes, the cultured products thereof and/or the processed products thereof.

13. A method for decomposing plastic according to any one of claims 9, 10 or 12, wherein the Basidiomycetes is wood rot Basidiomycetes.

14. A method for decomposing plastic according to claim 13, wherein said wood rod Basidiomycetes is white rot Basidiomycetes.

15. A method for decomposing plastic according to claim 14, wherein the white rot Basidiomycetes is strain NK-1148.

16. A method for decomposing plastic according to claim 14, wherein the white rot Basidiomycetes is *Porodisculus pendulus* NK-729W strain.

17. A plastic decomposing agent containing Basidiomycetes, the cultured products thereof and/or the processed products thereof.

18. A plastic decomposing agent according to claim 17, wherein the Basidiomycetes is strain NK-1148.

19. A method for decomposing plastic according to claim 17, wherein the Basidiomycetes is *Porodisculus pendulus* NK-729W strain.

* * * * *